United States Patent [19]
Edelman et al.

[11] Patent Number: 5,876,397
[45] Date of Patent: Mar. 2, 1999

[54] REDUCTION OF AN ARTERIOSCLEROTIC LESION BY SELECTIVE ABSORPTION OF ELECTROMAGNETIC ENERGY IN A COMPONENT THEREOF

[75] Inventors: William Edelman, Seal Beach; Robert F. Rosenbluth, Laguna Niguel; Dennis Constantinou, Irvine, all of Calif.

[73] Assignee: Boston Scientific Corporation, Natick, Mass.

[21] Appl. No.: 953,329

[22] Filed: Sep. 29, 1992

Related U.S. Application Data

[63] Continuation of Ser. No. 573,448, Jan. 24, 1984, abandoned.

[51] Int. Cl.$^6$ .................................................. A61B 17/36
[52] U.S. Cl. ...................................... 606/3; 606/7; 606/15
[58] Field of Search ........................................ 606/3, 7, 15

[56] References Cited

U.S. PATENT DOCUMENTS

| | | | |
|---|---|---|---|
| 3,327,712 | 6/1967 | Kaufman et al. | 128/398 |
| 3,565,062 | 2/1971 | Kurtz | 128/24 |
| 3,693,623 | 9/1972 | Harte et al. | 128/303.1 |
| 3,703,176 | 11/1972 | Vassiliadis et al. | 128/395 |
| 3,720,213 | 3/1973 | Hobart et al. | 128/395 |
| 3,750,670 | 8/1973 | Palanos et al. | 128/303.1 |
| 3,769,963 | 11/1973 | Goldman et al. | 128/2 R |
| 3,858,577 | 1/1975 | Bass et al. | 128/8 |
| 3,884,236 | 5/1975 | Krasnov | 128/303.1 |
| 4,120,293 | 10/1978 | Muckerheide | 128/2 A |
| 4,126,136 | 11/1978 | Auth et al. | 128/303.1 |
| 4,207,874 | 6/1980 | Choy | 128/303.1 X |
| 4,273,535 | 6/1981 | Yamamoto et al. | 433/216 |
| 4,316,467 | 2/1982 | Muckerheide | 128/303.1 |
| 4,388,924 | 6/1983 | Weissman et al. | 128/303.1 |
| 4,408,602 | 10/1983 | Nakajima | 128/303.1 |
| 4,414,059 | 11/1983 | Blum et al. | 156/659.1 |
| 4,417,948 | 11/1983 | Mayne-Banton et al. | 156/643 |
| 4,418,688 | 12/1983 | Loeb | 128/6 |
| 4,445,892 | 5/1984 | Hussein | 128/303.1 X |
| 4,448,188 | 5/1984 | Loeb | 128/6 |
| 4,461,294 | 7/1984 | Baron | 128/303.1 |
| 4,470,407 | 9/1984 | Hussein | 128/6 |
| 4,512,762 | 4/1985 | Spears | 604/21 |
| 4,614,190 | 9/1986 | Stanco | 128/395 |
| 4,622,953 | 11/1986 | Gordon | 128/1.3 |
| 4,665,913 | 5/1987 | L'Esperance | 128/303.1 |
| 4,732,148 | 3/1988 | L'Esperance | 128/303.1 |
| 4,765,330 | 8/1988 | Bach | 128/303.1 |
| 4,784,135 | 11/1988 | Blum et al. | 128/303.1 |
| 4,798,204 | 1/1989 | L'Esperance | 128/303.1 |
| 4,800,876 | 1/1989 | Fox et al. | 128/303.1 |

FOREIGN PATENT DOCUMENTS

| | | | |
|---|---|---|---|
| WO8502532 | 6/1985 | WIPO | A61B 17/36 |
| 8301893 | 6/1993 | WIPO . | |

OTHER PUBLICATIONS

Abela et al, "Effects of Carbon Dioxide . . . Plaques", Am. J. Card., vol. 50, No. 6, Dec. 1982, pp. 1199–1205 (Copy 128/303.1).

Trokel et al, "Excimer Laser Surgery . . . ", Am. J. Opth., 96:710–715, Dec. 1983. (Copy 128/303.1).

Taboada et al, "Responses . . . Laser Pulses", Health Physics, vol. 40, May 1981, pp. 677–683. (Copy 128/303.1).

Anders et al, "Investigation . . . Dye Lasers", Conf: Laser 77 Opto–Electronics, Munich, Ger. 20–24 Jun. 1977 pp.520–566. (Copy 128/395).

(List continued on next page.)

*Primary Examiner*—Lee Cohen
*Attorney, Agent, or Firm*—Charles J. Knuth; Peter C. Richardson; Lawrence C. Akers

[57] ABSTRACT

A novel method for reducing an arteriosclerotic lesion is disclosed in which the electromagnetic energy directed at the lesion is selectively absorbed by a lesion component, e.g. cholesterol. The resulting decomposition of said lesion component leads to reduction of the lesion with minimal risk of damage to blood constituents and adjacent healthy blood vessel tissue. Preferably, monochromatic electromagnetic energy is generated by a laser and is conducted to the vicinity of the lesion by at least one optical fiber.

10 Claims, 4 Drawing Sheets

OTHER PUBLICATIONS

Kassler, J., "Researchers Try Using Lasers to Unclog Arteries in Heart", *The New York Times*, p. C2 (Oct. 25, 1983).
"Laser Research: UV Beam Etches without Heat Effects", *Chemical and Engineering News*, pp. 4–5 (Jun. 13, 1983).
Free, "Heatless Laser Etching", Popular Science, Dec. 1983, p. 114. (Copy 128/303.1).
*News Spectra*, Jul. 1983, "IBM's Heatless Laser Etching" A Hot IC and Medical Prospect (Copy 128/303.1).
Lee et al, "The Qualitative Effects of Laser...", Am. H. J., Jun. 1983, vol. 105, No. 6, pp. 885–889. (Copy 128/303.1).

REDUCTION OF AN ARTERIOSCLEROTIC LESION BY SELECTIVE ABSORPTION OF ELECTROMAGNETIC ENERGY IN A COMPONENT THEREOF

This is a continuation of application Ser. No. 06/573,448, filed on Jan. 24, 1984, now abandoned.

BACKGROUND OF THE INVENTION

The regretably common disease atherosclerosis, which is a type of arteriosclerosis, is characterized by the formation of atherosclerotic lesions (also known as atherosclerotic plaques) on the inner wall of the aorta and the large and medium-sized arteries. The most important symptom in the early stages of this disease is hypertension. If uncorrected, however, the disease can lead to total blood vessel blockage, and ultimately, death of the patient. The atherosclerotic lesions are masses of fatty material associated with fibrous connective tissue, very often with secondary deposits of calcium salts and blood constituents. Human atherosclerotic lesions are characterized by a large lipid content, which may account for as much as 60 percent of the dry weight of some advanced lesions. Three major classes of lipids are found, i.e. cholesterol, cholesterol esters and phospholipids.

One surgical technique currently practiced for correcting problems arising from arteriosclerotic lesions is coronary or peripheral arterial bypass surgery, in which a blood vessel segment removed from another part of the patient's body, e.g. a saphenous vein segment, or a synthetic vascular graft is implanted in parallel with the occluded artery. Although arterial bypass surgery has been practiced with great success for many years, it is a major surgical operation with inevitable attendant risks and the medical profession is therefore continuously searching for more conservative techniques for reducing vascular obstructions such as arteriosclerotic lesions without bypass surgery.

Another surgical technique currently practiced with considerable success in the treatment of arteriosclerosis is transluminal angioplasty, in which a balloon catheter is inserted into an affected blood vessel and the balloon then expanded outwardly against the occlusion to recannulate the vessel. One disadvantage of this technique is that it cannot be employed when the vessel is already fully blocked (or almost so) by occlusions. Also, its practice results principally in redistribution (i.e. compaction) rather than physical or chemical removal of the lesion material, most of which remains in the affected blood vessel wall and can serve as a site for future occlusive growth.

Recently it has been proposed to reduce vascular occlusions such as arteriosclerotic lesions by the practice of laser revascularization angioplasty, in which electromagnetic energy generated by a laser is carried by one or more optical fibers to the vicinity of the occlusion and directed at the occlusion. Uptake of the laser energy by occlusion material results in its conversion to relatively low molecular weight organic substances, which are dissolved into and carried away by the blood stream. Suitable apparatus for the practice of laser revascularization angioplasty are disclosed in U.S. Pat. No. 4,207,874; U.S. Pat. No. 4,418,688; World Published Patent Application 8301893, published Jun. 9, 1983; World Published Patent Application 8303188, published Sep. 29, 1983 and World Published Patent Application 8302885, published Sep. 1, 1983. A highly significant advantage of laser revascularization angioplasty is that its practice can result in the essentially complete removal of a vascular occlusion (e.g. an arteriosclerotic lesion) in a surgical procedure that is far less invasive than bypass surgery. However, because of the difficulty in designing a laser catheter system whose use assures that the laser beam is carefully directed to impinge only upon the undesired occlusion, the practice of this technique involves a risk of damage to blood constituents and healthy surrounding tissues, particularly the surrounding non-arteriosclerotic blood vessel tissue.

SUMMARY OF THE INVENTION

It is an object of the present invention to provide an improved method for surgically reducing an arteriosclerotic lesion in a blood vessel of a patient by directing sufficient electromagnetic energy at said lesion to reduce it, in which improved method the lesion can be reduced without significant risk of damage to surrounding blood and healthy tissues.

This and other objects are achieved when essentially all of the electromagnetic energy directed at the lesion is of a wavelength in the ultraviolet or visible region at which energy is selectively absorbed, as compared to absorption by whole blood and non-arteriosclerotic blood vessel tissue, by a lesion component present in said lesion at a greater weight percentage (on a dry basis) than in the whole blood or surrounding non-arteriosclerotic blood vessel tissue of the patient. The ensuing reaction and decomposition of said lesion component leads directly to the reduction of the lesion without significant risk of damage to the vicinal blood or, should the electromagnetic energy be inadvertently misdirected, to the surrounding healthy tissues. The electromagnetic energy directed at the lesion is preferably monochromatic, i.e. essentially all within an extremely narrow wavelength range. Preferably, monochromatic electromagnetic energy is generated by a laser and conducted to the vicinity of the lesion by at least one optical fiber. Monochromatic ultraviolet energy is preferably generated by an excimer laser. However, the electromagnetic energy need not necessarily be conducted to the lesion site by optical fibers. Thus, for example, one or more beams of energy might be directed from exterior locations through the patient's skin to the location of the lesion.

In one embodiment of the novel method, electromagnetic energy having a wavelength of about 248 nanometers is directed at an arteriosclerotic lesion containing cholesterol as a component thereof. Cholesterol in the lesion selectively absorbs and is activated by this energy, thereby leading to the reduction of the lesion.

As used herein, the term "reducing an arteriosclerotic lesion", or the like, means substantially reducing the size of the lesion. Preferably, of course, treatment is continued until essentially complete removal of the lesion has been achieved.

BRIEF DESCRIPTION OF THE INVENTION

The present invention will be described in detail with reference to certain preferred embodiments thereof. Reference to these embodiments does not limit the scope of the invention, which is limited only by the scope of the claims:

DETAILED DESCRIPTION OF THE INVENTION

Figure 1:
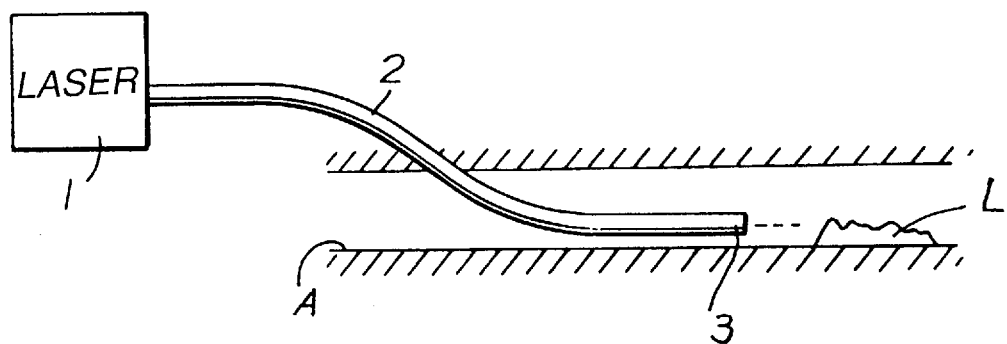
FIGS. 1 to 3 illustrate apparatus suitable for use in the practice of the present invention.

At the heart of laser revascularization angioplasty is the reduction of a vascular occlusion by the chemical reaction and decomposition of occlusion components. As the impinging laser energy is absorbed, occlusion material reactants in the immediate vicinity of the point of impingement are heated to a substantially increased temperature until they are kinetically activated to react and decompose. The occlusion is progressively reduced within a surgically reasonable time, e.g. within a few hours at the most. In the practice of prior art methods in which the electromagnetic energy is not selectively absorbed by a component of the undesired occlusion, inadvertant misdirection of this energy at surrounding healthy tissue can result in significant damage to that tissue. The locus of this damage can provide a site for the formation of a thrombus or a new lesion; in extreme situations unintended damage to surrounding healthy tissue could lead to a false aneurysm. Additionally, significant damage to blood constituents, e.g. hemolysis, can result from the passage of the electromagnetic energy through the patient's blood.

In the practice of the present invention, essentially all of the electromagnetic energy directed at the lesion sought to be reduced is of a wavelength at which energy is selectively absorbed, as compared to absorption by whole blood and non-arteriosclerotic blood vessel tissue, by a lesion component present in said lesion at a greater weight percentage (dry basis) than in the whole blood or surrounding non-arteriosclerotic blood vessel tissue of the patient. Electromagnetic energy passing through the patient's blood or inadvertently directed at healthy tissue will tend to be transmitted or reflected, rather than absorbed, thereby. Since neither reflection nor transmission leads to substantial heating, any significant risk of damage to the patient's blood or healthy tissues is eliminated. Consequently, it is not necessary to stop the flow of blood through the affected vessel while directing energy at the lesion, and the design of the apparatus utilized to direct said energy (e.g. a laser catheter system with viewing and positioning means) to the lesion becomes much less critical. The feasibility of achieving essentially complete removal of the lesion, which is of course preferred over a merely partial removal, is greatly enhanced because the electromagnetic energy beam can be repeatedly passed over the lesion-healthy tissue boundary at the bottom and sides of the lesion site without significant risk of damaging the healthy tissue. Also, lower total energy input to the patient's body is required than when non-selectively absorbed electromagnetic energy is utilized. As a minimum however, for satisfactory results in the practice of the invention, the electromagnetic energy must be made to impinge upon the arteriosclerotic lesion tissue at a rate of at least about 0.5 watts.

An important feature of the practice of the present invention is that the selectively absorbing lesion component acts as an energy sink for the electromagnetic energy directed at the lesion. Molecules of this lesion component in the region of impingement of the electromagnetic energy upon the lesion absorb electromagnetic energy and are consequently heated until they react and decompose. The heating, reaction and decomposition of the selectively absorbing component or components triggers in turn, through various heat transfer and chemical reaction mechanisms, the heating, reaction and decomposition of the other (non-selectively absorbing) lesion components in the immediate vicinity of the point of impingement of the electromagnetic energy. Tissue matter displaced from the immediate vicinity of the point of impingement of the electromagnetic energy upon the lesion is unaffected thereby.

Another important feature of the present invention is that the electromagnetic energy directed at the lesion is in the ultraviolet or visible region of the spectrum. Energy absorption by a substance in the ultraviolet or visible region is as a general rule associated with gross configurational changes in the molecular structure of the substance (e.g., cis-trans isomerization) as well as with rotational or vibratory molecular movements. Such gross configurational change electromagnetic energy absorption peaks are more widely spaced and more specific to particular substances than are the higher wavelength absorption peaks associated only with rotational and vibratory molecular movements. Thus, the likelihood of finding a clearly discernible wavelength or band of wavelengths outside of the ultraviolet and visible region at which selective energy absorption by a lesion component occurs is very small.

One significant arteriosclerotic lesion component is cholesterol, which exhibits an electromagnetic energy absorption peak in the ultraviolet region at a wavelength of from about 244 to about 250 nanometers, depending upon on its environment. The ensuing chemical reaction and decomposition of cholesterol, which is accompanied by a visible fluorescence, leads to a reduction of the arteriosclerotic lesion. The absorption of the ca. 244 to ca. 250 nanometers wavelength light by cholesterol is highly selective as compared to whole blood and healthy human blood vessel tissue, which exhibit no electromagnetic energy absorption peaks at or near that wavelength. The existence of selective absorption characteristics of an arteriosclerotic lesion component can be determined from a few simple experiments, as will be illustrated below in the case of cholesterol.

When it is desired to practice the present invention by activating cholesterol with electromagnetic energy selectively absorbed thereby, said energy is preferably generated by a krypton/fluorine excimer laser such as a Tachisto Model 800 XR Krypton/Fluorine Excimer Laser (Tachisto Inc.; Needham, Mass.). A wavelength of 248 nanometers is obtained by using in the laser discharge chamber a gas mixture of 0.26 mole percent F, 4.35 mole percent Kr, 39.13 mole percent Ne, balance He. The skilled worker in the art will recognize that this laser output wavelength can be readily varied, within the range of from about 200 nanometers to about 300 nanometers, if desired for selective absorption by a different lesion component, by replacing the krypton or fluorine with another gas.

Figure 2:
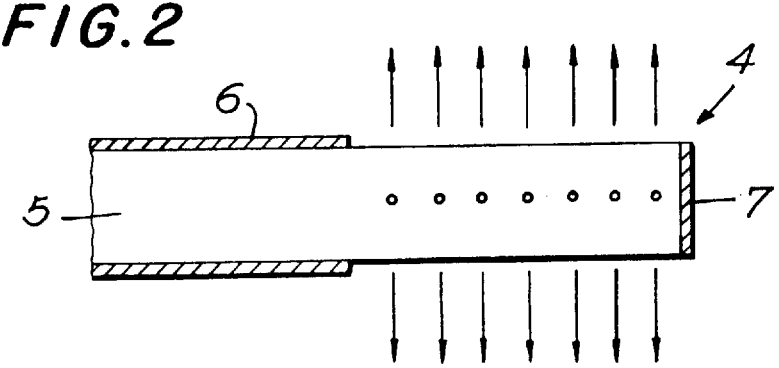
Figure 3:
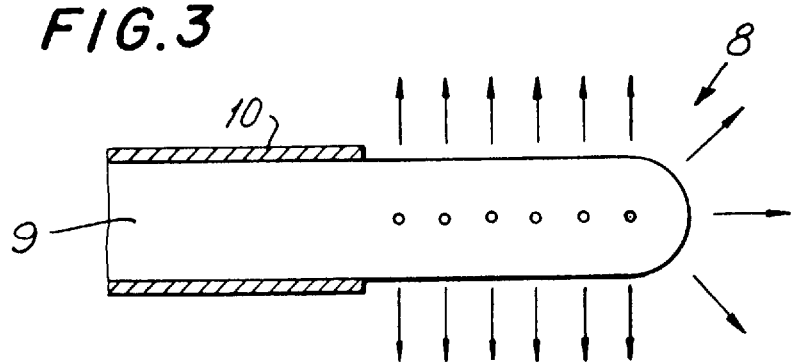

When electromagnetic energy of any suitable wavelength is generated by a laser, that energy is preferably conducted to the vicinity of the arteriosclerotic lesion sought to be reduced by one or more optical fibers. These fibers may be carried in, and extend to the distal end of, a catheter that may also contain means for illuminating and viewing the inside of the affected blood vessel, means connected to a suction source for withdrawing lesion debris, and means for irrigation of the treated region. In use, the distal tip of the catheter may be properly positioned relative to the lesion sought to be reduced by known means such as endoscopic viewing or fluoroscopy. A fixed focal point for the laser energy may be realized by providing a plurality of laser energy-conducting optical fibers circumferentially-distributed around the transverse cross-section of a cylindrical catheter, with the distal tips of the fibers bent to form together a frusto-conical configuration or each bevelled at an angle ranging up to about 60° relative to the fiber axis. Preferably, the optical fibers employed with a laser catheter in the practice of the present invention are fused silica fibers having a core diameter of from about 100 microns to about 600 microns. The surface of each fiber may optionally be buffed for a length of from about 0.01 cm. to about 5 cm. from its distal tip. The particular design and configuration of the optical fiber or fibers and optical fiber-carrying catheter are not critical to the practice of the present invention, as broadly contemplated. Thus, two designs of suitable single self-supporting optical fibers 4 and 8 that may be employed in the practice of the present invention with a laser but without a laser catheter or other optical fibers are depicted in FIGS. 2 and 3. In FIG. 2, optical fiber core 5 is covered with cladding 6 (shown in section) along the vast majority of its length and is also covered with cladding 7 (shown in section) at its distal tip. However, a short length of core 5 at its distal end is left unclad, thereby providing for radial, but not axial, emission of energy. In FIG. 3, optical fiber core 9 is covered with cladding 10 (shown in section) along the vast majority of its length. However, a short length of core 9 at its distal end as well as its rounded distal tip (which may be formed by heating) is left unclad, thereby providing for radial and axial emission of energy. Fiber 8 may be utilized to reduce highly advanced lesions that essentially totally block the affected vessel as well as less advanced lesions that leave space for passage of the distal end of the fiber (and also, of course, blood). Fiber 4 can only be used in the latter situation. The small circles at the distal ends of fibers 4 and 8 in FIGS. 2 and 3 depict the emission of electromagnetic energy toward the viewer.

FIG. 1 is a drawing of an apparatus suitable for use in the practice of the present invention. Electromagnetic energy of appropriate wavelength is generated in an extracorporeal laser 1 and conducted by one or more optical fibers carried in a hollow lumen laser catheter 2. The optical fiber or fibers extend to the distal end 3 of catheter 2, from which distal end 3 the electromagnetic energy is emitted and directed at the arteriosclerotic lesion sought to be reduced.

The surgical procedure for the use of the apparatus schematically depicted in FIG. 1 will be described with reference to the reduction of an atherosclerotic lesion in the iliac artery. This procedure can of course be readily adapted to the reduction of lesions in other blood vessels. After local anesthesia has been administered to the patient percutaneously, a rigid hollow needle is inserted into the iliac artery A downstream of the lesion L, a guide wire is inserted through the needle into the artery and the needle is removed. An introducer comprising an inner part adapted to closely fit over the guide wire and a tubular outer sheath is then inserted over the guide wire into the artery, after which said inner part is withdrawn leaving the introducer outer sheath in place. A guiding catheter is then inserted through the outer sheath and properly positioned with its distal end in the vicinity of the lesion by means of fluoroscopic viewing of a contrast medium injected through the guiding catheter. The guide wire is then removed. Finally, the laser catheter 2 is inserted through the guiding catheter and its distal end properly positioned immediately downstream of the lesion by means of fluoroscopic viewing of a contrast medium injected through the guiding catheter. The laser 1 is then activated and a laser beam emitted at the lesion from the distal end 3 of catheter 2. The impingement of the laser beam on the lesion body is continued until an essentially complete removal of the lesion material has been accomplished.

Figure 7:
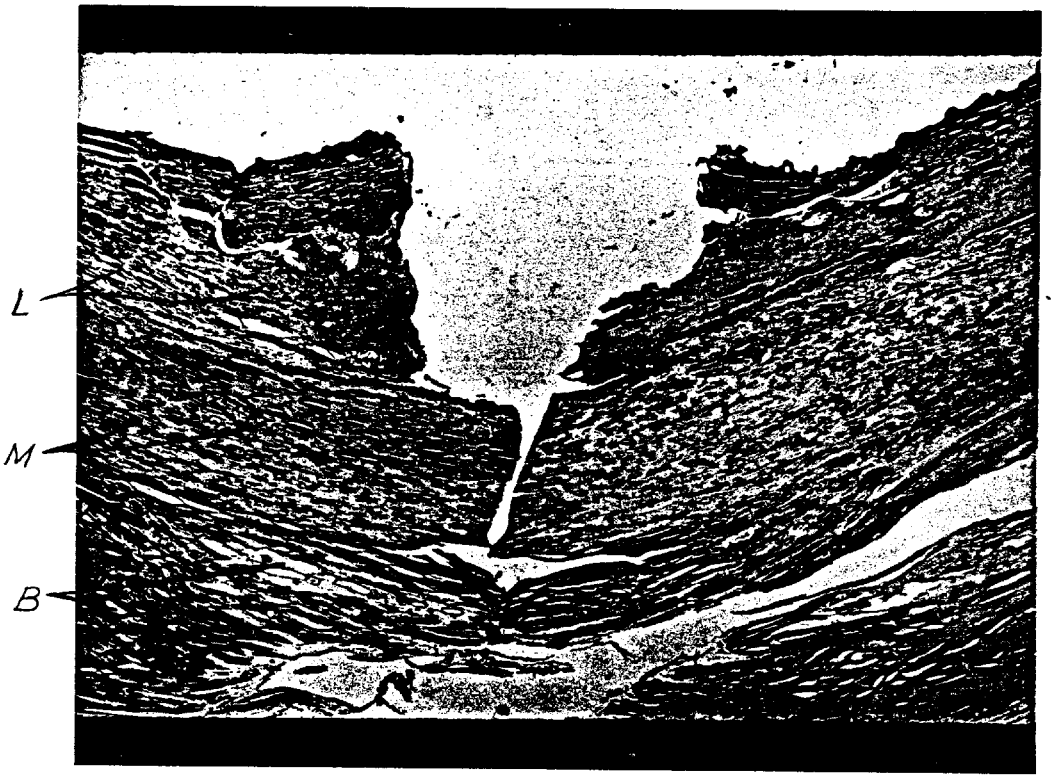
FIGS. 7 and 8 are photographs depicting the highly successful reduction of an arteriosclerotic lesion by means of the practice of the present invention, and the negligible effect on healthy blood vessel tissue.
Figure 8:
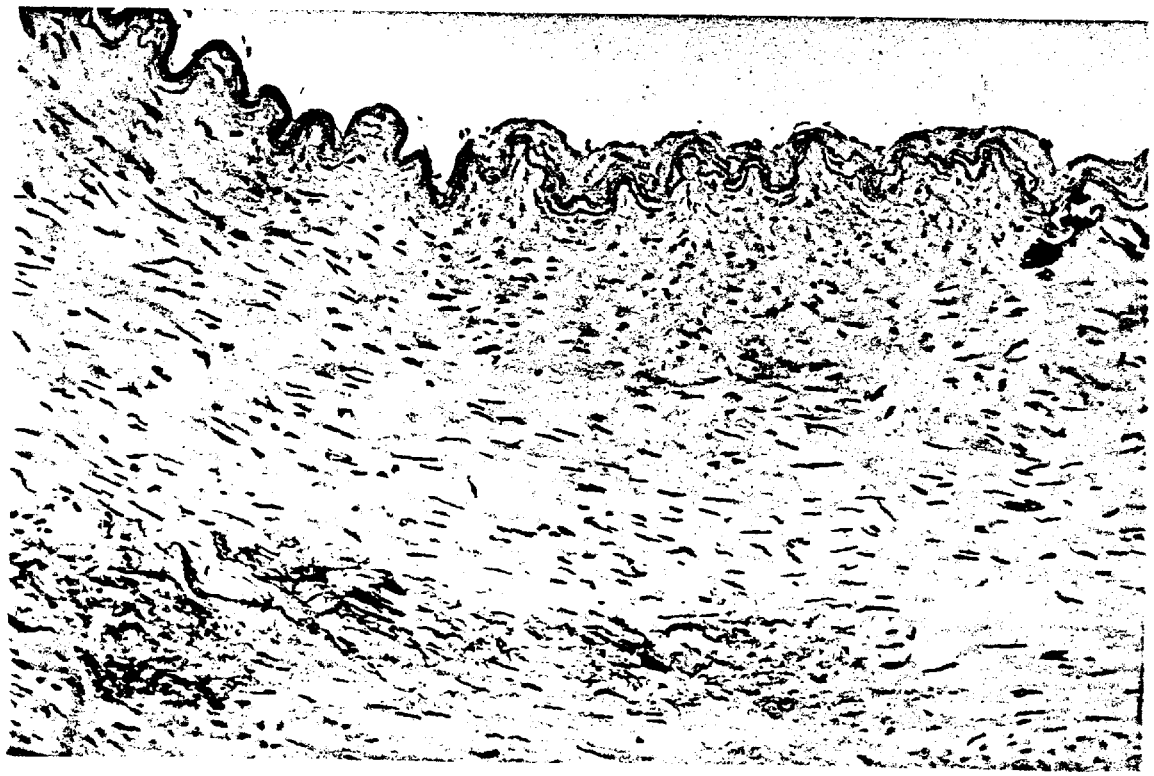

FIG. 7 is a photograph showing the effect of a 30 watts beam of 248 nm. electromagnetic energy (generated by a Tachisto Model 800 XR Krypton/Fluorine Excimer Laser) directed in vitro for 15 seconds at an advanced arteriosclerotic lesion in a human iliac artery segment. The beam of energy readily drilled away the lesion material but did not penetrate the underlying non-arteriosclerotic tissue. In FIG. 7, L is the lesion, M is the non-arteriosclerotic media and B is the non-arteriosclerotic adventitia. The thin cut through the media below the large empty space in the lesion formed by the energy beam is an artifact of histology. FIG. 8 is a photograph of a healthy non-arteriosclerotic human iliac arterial wall taken after it had been irradiated in vitro by a beam of 248 nm. electromagnetic energy of an intensity sufficient to reduce an arteriosclerotic lesion. The small dark spots in FIG. 8 are the nuclei of healthy cells. As can be seen, the impinging energy beam had negligible adverse effect on the healthy arterial wall tissue.

EXAMPLE 1

Determination of Absorption Peak for Cholesterol

Figure 4:
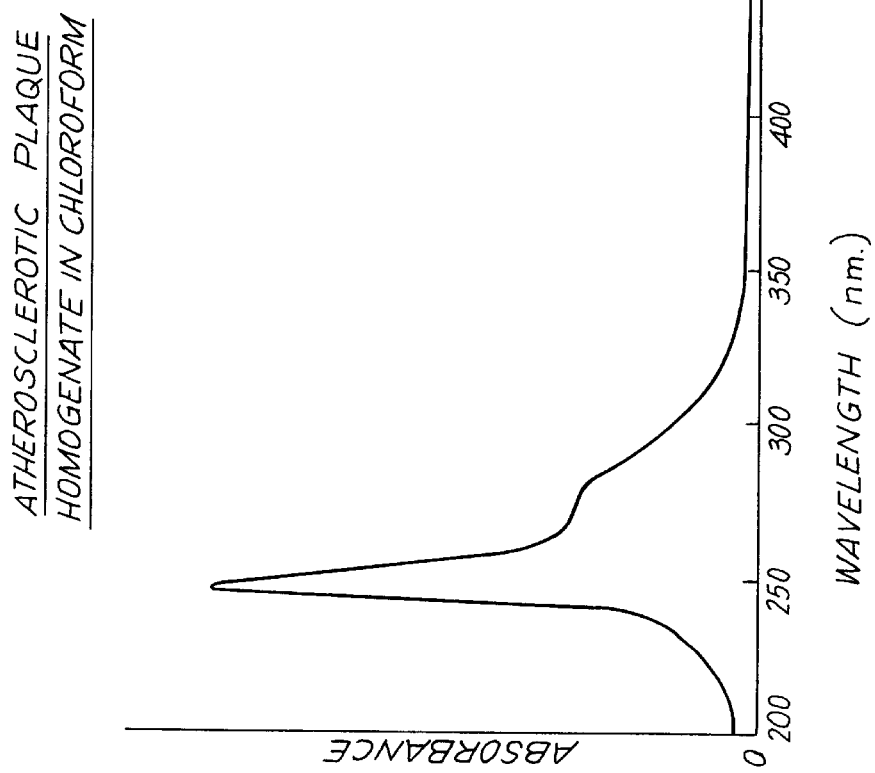
FIGS. 4 to 6 show the absorption of electromagnetic energy by cholesterol, atherosclerotic lesion material, hemolyzed blood and blood plasma as a function of wavelength.

The maximum absorptivity of cholesterol was determined by prepraing a 10 g/l stock solution of U.S.P. grade cholesterol in spectral grade chloroform. This stock solution was placed in the sample cell of an ultraviolet spectrophotometer and pure spectral grade chloroform in the reference cell. The absorbance spectra for cholesterol was then obtained and plotted by the spectrophotometer over the range from 400 nm. to 200 nm. at ambient temperature (see FIG. 4). A highly pronounced absorption peak was exhibited at about 250 nm.

EXAMPLE 2

Determination of Absorption Peaks in Atherosclerotic Lesion Material

Figure 5:
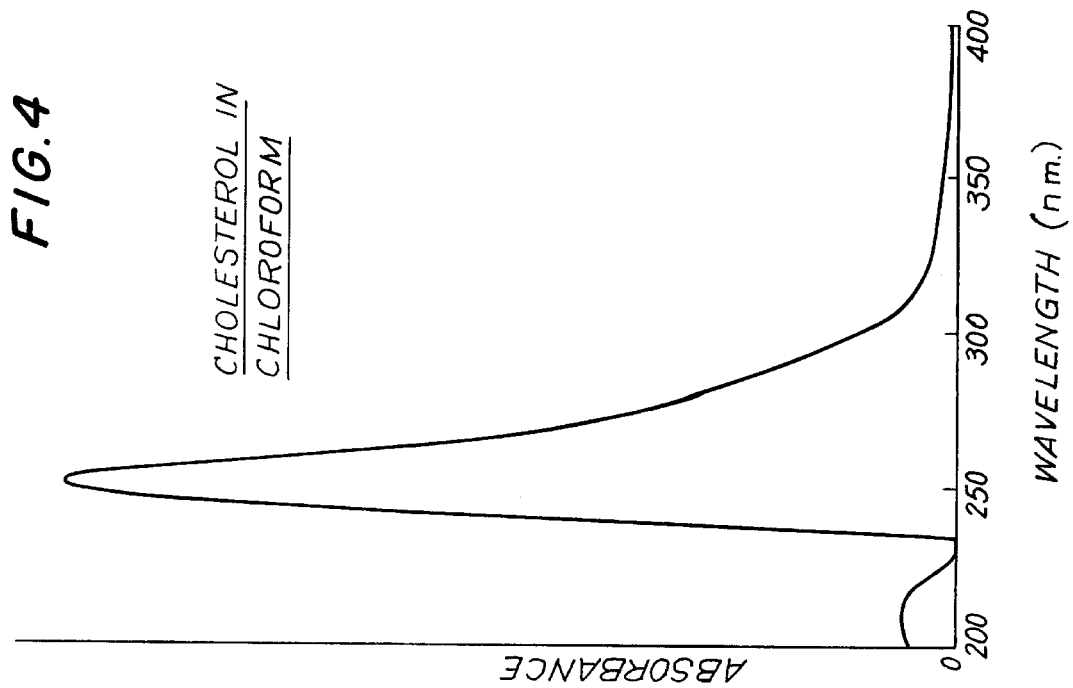

A 0.5 cm. long length of human advanced atherosclerotic iliac artery was cut and the atherosclerotic plaque material carefully dissected therefrom. This plaque material was added to 1 ml. spectral grade chloroform and the resulting mixture homogenized until a cloudy suspension was obtained. An aliquot of this suspension was diluted with spectral grade chloroform, and the diluted sample scanned in the ultraviolet spectrophotometer (vs. pure spectral grade chloroform) for absorbance in the range from 500 nm. to 200 nm. at ambient temperature (see FIG. 5). A highly pronounced absorption peak correlating with the presence of cholesterol was exhibited at about 244 nm., while a pronounced shoulder-type of peak not attributable to the presence of cholesterol was exhibited at about 275 nm.

EXAMPLE 3

Determination of Absorption Peaks in Hemolyzed Blood and Blood Plasma

Figure 6:
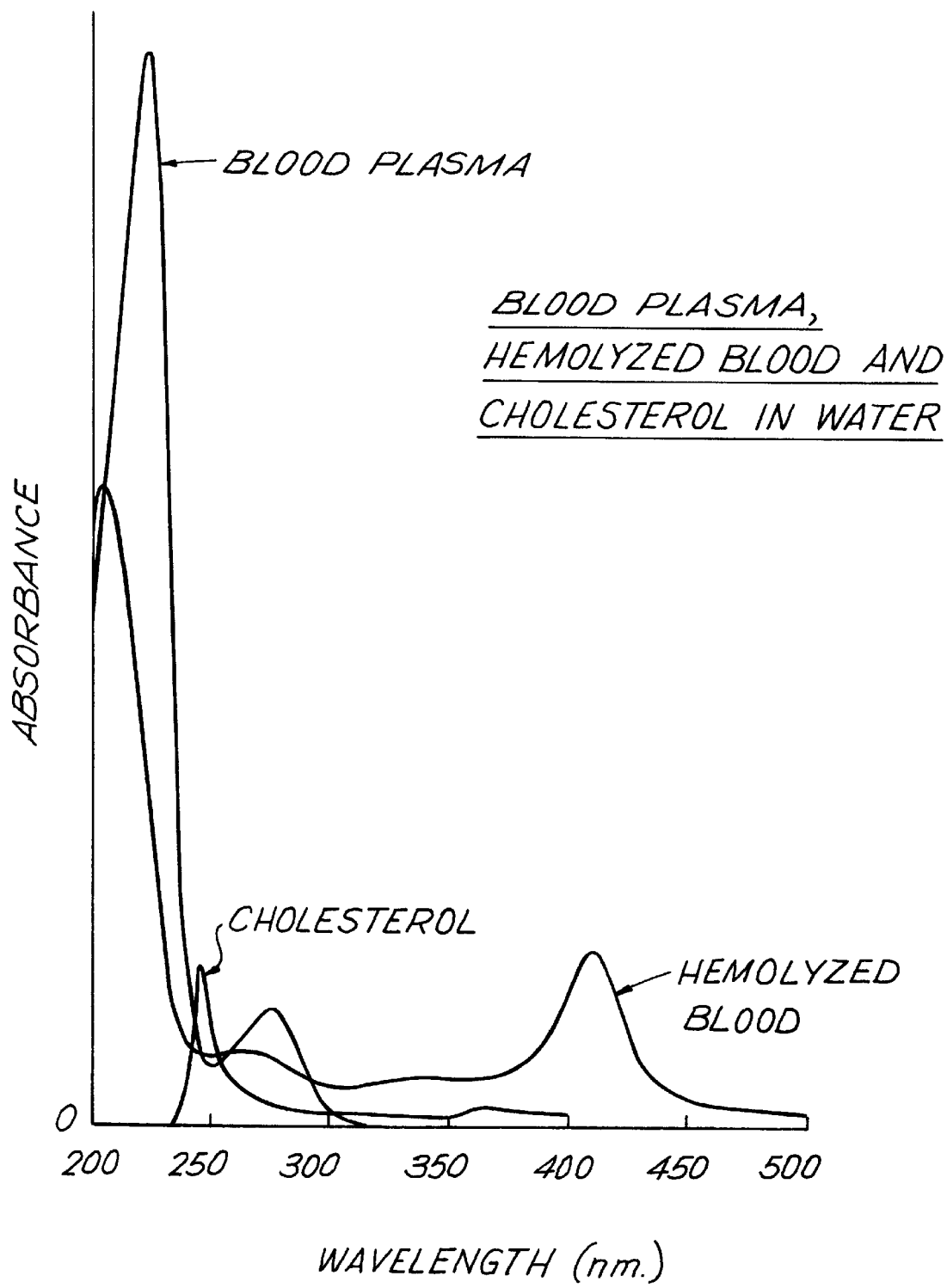

Samples of human blood plasma, hemolyzed whole human blood and U.S.P. grade cholesterol were diluted with distilled water and the absorption spectra of the resulting three solutions obtained sequentially (vs. normal saline solution in the reference cell) over the range from 500 nm. to 200 nm. at ambient temperature (see FIG. 6). The cholesterol sample exhibited an absorption peak at about 244 nm. to 245 nm., while neither blood sample exhibited an absorption peak anywhere near this value. This result clearly establishes the selective absorption by cholesterol, in comparision with the surrounding media, of electromagnetic energy at wavelengths of from about 240 nm. to about 255 nm.

We claim:

1. A method for reducing an arteriosclerotic lesion in a blood vessel of a patient which comprises directing sufficient electromagnetic energy at said lesion to reduce it, with essentially all of said electromagnetic energy directed at said lesion being of a wavelength in the ultraviolet region at which energy is selectively absorbed, as compared to absorption by whole blood and non-arteriosclerotic blood vessel tissue, by a lesion component present in said lesion at a greater weight percentage (dry basis) than in the whole blood or surrounding non-arteriosclerotic blood vessel tissue of the patient.

2. The method of claim 1 wherein said wavelength is from about 200 nanometers to about 300 nanometers.

3. The method of claim 1 wherein said lesion component is present in said lesion at no less than about 1 percent of the total weight of said lesion on a dry basis.

4. The method of claim 3 wherein said lesion component is present in said lesion at no less than about 5 percent of the total weight of said lesion on a dry basis.

5. The method of claim 1 wherein said lesion component is cholesterol and essentially all of said electromagnetic energy directed at said lesion is of a wavelength of about 248 nanometers.

6. The method of claim 5 wherein said electromagnetic energy is generated by a krypton/fluorine excimer laser and conducted to the vicinity of said lesion by at least one optical fiber.

7. The method of claim 6 wherein said optical fiber is a fused silica optical fiber having a core diameter of from about 100 microns to about 600 microns.

8. The method of claim 1 wherein said electromagnetic energy directed at said lesion is monochromatic.

9. The method of claim 8 wherein said electromagnetic energy is generated by a laser and conducted to the vicinity of said lesion by at least one optical fiber.

10. The method of claim 9 wherein said laser is an excimer laser.

* * * * *